US00PP30169P2

(12) United States Plant Patent
Korlipara

(10) Patent No.: US PP30,169 P2
(45) Date of Patent: Jan. 29, 2019

(54) ***ECHINACEA* PLANT NAMED 'TNECHPG'**

(50) Latin Name: ***Echinacea* spp.**
Varietal Denomination: TNECHPG

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/932,017

(22) Filed: Jan. 25, 2018

(51) Int. Cl.
*A01H 5/02* (2018.01)

(52) U.S. Cl.
USPC ..... Plt./428

(58) Field of Classification Search
USPC ..... Plt./428
See application file for complete search history.

*Primary Examiner* — Annette H Para
(74) *Attorney, Agent, or Firm* — Klarquist Sparkman, LLP

(57) ABSTRACT

A new and distinct *Echinacea* plant named 'TNECHPG' is provided, characterized by soft orange to soft pink multicolored flowers, an amazing number of inflorescences starting in the first season, a very compact habit, very long bloom time with excellent rebloom, ray florets held horizontally, and excellent vigor.

1 Drawing Sheet

Botanical denomination: *Echinacea* spp.
Variety designation: 'TNECHPG'.

BACKGROUND OF THE INVENTION

The present invention relates to a new and distinct cultivar of *Echinacea* and given the cultivar name 'TNECHPG'. *Echinacea* is in the family Asteraceae. The new cultivar is part of a planned breeding program for a landscape series with very compact habits and profuse inflorescences. The exact parents of this selection are unknown, unnamed, proprietary interspecific hybrids bred from *Echinacea paradoxa, Echinacea purpurea,* and *Echinacea tennesseensis.*

Compared to *Echinacea* 'Big Kahuna' (U.S. Plant Pat. No. 26,159), the new cultivar is much shorter and the inflorescences are smaller.

This new *Echinacea* cultivar is uniquely distinguished by:

1. soft orange to soft pink multicolored ray florets,
2. an amazing number of inflorescences starting in the first season,
3. a very compact habit,
4. very long bloom time with excellent rebloom,
5. ray florets held horizontally, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a two-year-old *Echinacea* 'TNECHPG' growing in the trial field in full sun in early September in Canby, Oreg.

DETAILED PLANT DESCRIPTION

The following is a detailed description of the new *Echinacea* cultivar based on observations of 9-month-old specimens growing in the trial field in full sun in Canby, Oreg. Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The color descriptions are all based on The *Royal Horticultural Society Colour Chart,* 5$^{th}$ edition, 2007.

Plant:

*Type*.—Herbaceous perennial.
*Hardiness*.—USDA Zones 4 to 9.
*Size*.—Grows to 32 cm wide and 40 cm tall to top of inflorescences.
*Form*.—Basal clump, with 4 to 7 stems from the base.
*Vigor*.—Excellent.
*Roots*.—Fibrous, with many downward growing and few laterals, ivory in color, Yellow White 158D, roots develop easily from cuttings from the crown.

Leaf (stem):

*Type*.—Simple.
*Shape*.—Lanceolate.
*Arrangement*.—Alternate.
*Blade size*.—Grows to 21 cm long (usually 14 cm long) and 3.3 cm wide.
*Margins*.—Entire.
*Apex*.—Acuminate.
*Base*.—Attenuate.
*Surface texture*.—Strigose on both sides.
*Venation*.—Pinnate, Yellow Green 145C on both sides.

*Color*.—Topside Green N137B, bottom side closest to Yellow Green 147B.

*Petiole description*.—Clasping, grows to 6 cm long and 3 mm wide, scabrous, narrow leafy edges which fold upwards, Yellow Green 146C.

Inflorescence:

*Type*.—Composite on terminal stalked heads.

*Flowering stem*.—Grows to 42 cm tall from the base of the plant to the terminal inflorescence and can grow to 11 cm long from the top stem leaf to the base of an inflorescence; unbranched to branched, with 1 to 6 inflorescences per stem; diameter growing to 6 mm wide near the inflorescence; strigose; Yellow Green 145C stippled 147C, with slight tints of Greyed Purple 187A in high light.

*Size*.—Grows to 9.5 cm wide and 6.5 cm deep as disc enlarges.

*Form*.—Ray florets held horizontally, curving down in old inflorescences, mature disc is conic.

*Immature inflorescence* (*bud*).—3.5 cm wide and 2 cm deep, ray florets held upright at 35 degree angle and rolled up so only the back color shows, Greyed Red 181B except tip Yellow Green 145C, disc color Green 137A with bracts Greyed Purple 187B.

*Ray florets*.—Without pistil or stamen, 20 to 31 in number, grow to 40 mm long and 14 mm wide, oblanceolate with the tip two-to-three-toothed (each acute), entire margins, base attenuate, glabrous on both sides; fully open florets topside Orange 26A blending to base Red 39A, bottom side Red 38B with streaks of Red Purple 60C; florets fade gradually to both sides Orange Red 35D with Red Purple 60C at base.

*Disc*.—Flat becoming conic, becoming 39 mm deep and 45 mm wide with maturity, Greyed Purple N186A in background with bracts Orange 26A with tips Greyed Purple 187A.

*Disc florets*.—About 400 in number, each with 1 pistil and 4 stamen, grow to 11 mm long and 2 mm wide, each with one persistent, very stiff linear bract (15 mm long with the top 1 mm Greyed Purple 187B blending to 4 mm Orange 24B to 5 mm Green 137A blending to White NN155A on bottom); corolla 5 mm long and 2 mm wide, tubular, 5 lobed, glabrous, Yellow Green 147B on lobes blending to 145C; pistil 10 mm long, ovary 3 mm long, White NN155D with top Yellow Green 144A, style 6 mm long White NN155A, 2-branched stigma spreading 3 mm wide, Greyed Purple 187B; stamen 5 mm long, filaments 2 mm long and White NN155B, anthers 3 mm long and Greyed Purple N186A, pollen, slight, Yellow 11B.

*Involucral bracts*.—In 4 leafy series, area grows to 38 mm wide and 10 mm deep, lobes lanceolate in shape, reflexed, grow to 10 mm long and 5 mm wide, Green N137A, margins strigose, tip acute, strigose on both sides.

*Receptacle*.—Grows to 17 mm wide and 25 mm deep, White NN155B.

*Bloom period*.—June through October in Canby, Oreg.

*Fragrance*.—Slight.

*Lastingness*.—Each inflorescence lasts about two weeks in Canby, Oreg.

Seeds: 3 mm long and 2.5 mm wide, oval, Brown 200C.

*Fertility*.—Poor.

Disease and pests: No pests or diseases have been observed on plants grown under commercial conditions in Canby, Oreg. No resistances are known.

I claim:

1. A new and distinct *Echinacea* plant as herein illustrated and described.

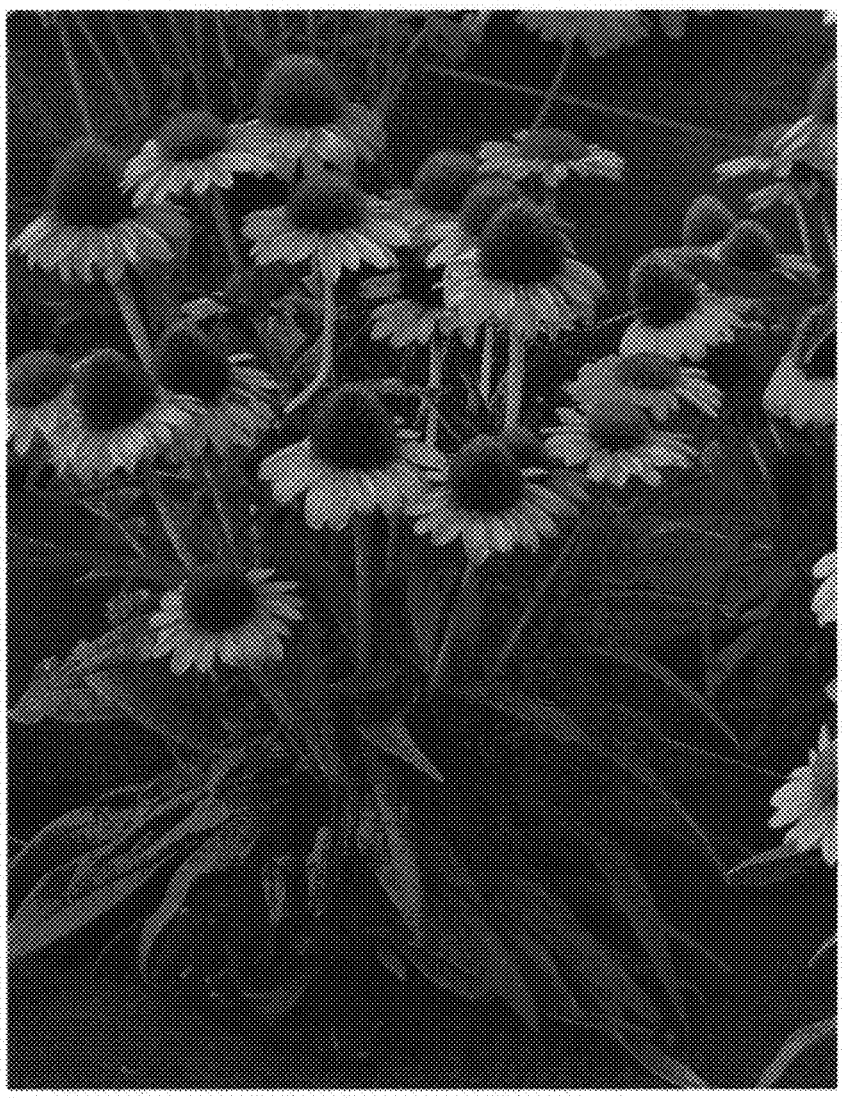

* * * * *